US008791138B2

(12) United States Patent
Seeman et al.

(10) Patent No.: US 8,791,138 B2
(45) Date of Patent: *Jul. 29, 2014

(54) COMPOSITIONS AND METHODS FOR ALLEVIATING DEPRESSION OR IMPROVING COGNITION

(75) Inventors: Philip Seeman, Toronto (CA); Philip M. Tokeikis, Vancouver (CA)

(73) Assignee: Clera Inc., Vancouver (CA)

( * ) Notice: Subject to any disclaimer, the term of this patent is extended or adjusted under 35 U.S.C. 154(b) by 579 days.

This patent is subject to a terminal disclaimer.

(21) Appl. No.: 12/863,513

(22) PCT Filed: Feb. 5, 2009

(86) PCT No.: PCT/CA2009/000145
§ 371 (c)(1),
(2), (4) Date: Jul. 19, 2010

(87) PCT Pub. No.: WO2009/097688
PCT Pub. Date: Aug. 13, 2009

(65) Prior Publication Data
US 2010/0298382 A1 Nov. 25, 2010

Related U.S. Application Data

(60) Provisional application No. 61/026,279, filed on Feb. 5, 2008.

(51) Int. Cl.
*A01N 43/40* (2006.01)
*A61K 31/445* (2006.01)

(52) U.S. Cl.
USPC .......................................... 514/327; 514/317

(58) Field of Classification Search
USPC ....................................................... 514/327
See application file for complete search history.

(56) References Cited

U.S. PATENT DOCUMENTS

| 7,273,888 | B2 * | 9/2007 | Ramesh et al. ............... | 514/564 |
| 2004/0156791 | A1 * | 8/2004 | Rabinowitz et al. ........... | 424/46 |
| 2006/0166965 | A1 | 7/2006 | Kapur et al. | |
| 2006/0167032 | A1 * | 7/2006 | Galer et al. ................... | 514/282 |
| 2007/0142399 | A1 | 6/2007 | Altar et al. | |

OTHER PUBLICATIONS

Chan et al. (A double-blind randomised comparison of risperidone and haloperidol in the treatment of behavioural and psychological symptoms in Chinese dementia patients, International Journal of Geriatric Psychiatry vol. 16, Issue 12, pp. 1156-1162, Dec. 2001).*
Csernansky et al. (Sensitization versus tolerance to the dopamine turnover-elevating effects of haloperidol: the effect of regular/intermittent dosing. Psychopharmacology (Berl). 1990;101(4):519-24.).*
Lin et al. (Onset of psoriasis during therapy with fluoxetine. General Hospital Psychiatry 32 (2010) 446.e9-446.e10).*
O'Sullivan et al. (Trichotillomania: Behavioral Symptom or Clinical Syndrome? Am J Psychiatry 154:10, Oct. 1997).*

Azima et al. ("The effect of R-1625 (Haloperidol) in mental syndromes: a multiblind study." American Journal of Psychiatry 117.6 (1960): 546-547).*
Cohen et al. (Behavioral Effects of Haloperidol in Young Autistic Children. J Am Acad Child Psychiatry. 1980 Autumn;19(4):665-77).*
Rico-Villademoros, Fernando; Hidalgo, Javier; Dominguez, Inmaculada; Garcia-Leiva, Juan Miguel; Calandre Pita, Elena, "Atypical antipsychotics in the treatment of fibromyalgia: a case series with olanzapine", Elsevier, Progress in Neuro-Psychopharmacology & Biology Psychiatry, 2005, 161-164.
Simon, Jeffrey S.; Nemeroff, Charles B.; "Aripiprazole Augmentation of Antidepressants for the Treatment of Partially Responding and Nonresponding Patients with Major Depressive Disorder", J. Clin. Psychiatry, 66:10, Oct. 2005, 1216-1220.
Shitij, Kapur; Zipursky, Robert; Jones, Corey; Remington, Gary; Houle, Sylvain; "Relationship Between Dopamine D2 Occupancy, Clinical Response, and Side Effects: A Double-Blind PET Study of First-Episode Schizophrenia", Am. J. Psychiatry, 157:4, Apr. 2000, 514-520.
Shitij, Kapur; Remington, Gary; Jones, Corey; Wilson, Alan, Dasilva, Jean; Houle, Sylvain, Zipursky, Robert; "High Levels of Dopamine D2 Receptor Occupancy With Low-Dose Haloperidol Treatment: A PET Study", Am. J. Psychiatry, 153:7, Jul. 1996, 948-950.
Mehler-Wex, Claudia; Romanos, Marcel; Kirchheiner, Julia; Schulze, Ulrike M.E.; "Atypical Antipsychotics in Severe Anorexia Nervosa in Children and Adolescents—Review and Case Reports", European Eating Disorders Review, Eur. Eat. Disorders Rev. 16, 2008, 100-108.
Philip, Noah S.; Carpenter, Linda L.; Tyrka, Audrey R.; Price, Lawrence H.; "Augmentation of Antidepressants with Atypical Antipsychotics: A Review of the Current Literature", Journal of Psychiatric Practice, vol. 14, No. 1., 2008, 34-44.
Mehler-Wex C. et al.: "Atypical Antipsychotics in Severe Anorexia Nervosa in Children and Adolescents—Review and Case Reports", European Eating Disorders, vol. 16, Jan. 2008, 100-108.
Wolfersdorf M et al.: "Pharmacotherapy of Delusional Depression: Experience with Combinations of Antidepressants with the Neuroleptics Zotepine and Haloperidol", Neuropsychobiology, vol. 29, Jan. 1994, 189-193.
European Extended Search Report, Nov. 24, 2011.
Pani, L. et al., "The substituted benzamides and their clinical potential on dysthymia and on the negative symptoms of schizophrenia", Molecular Psychiatry (2002) 7, 247-253.

(Continued)

*Primary Examiner* — Layla Soroush
(74) *Attorney, Agent, or Firm* — Bereskin & Parr LLP/S.E.N.C.R.L., s.r.l.; Patricia Folkins

(57) ABSTRACT

This application describes compositions of receptor inhibitors, including antipsychotic agents, for example haloperidol, and methods of use for alleviating clinical depression, improving cognition and/or treating other syndromes, conditions or diseases for which anti-depressant agents are prescribed. Furthermore, this application describes compositions and methods to induce supersensitivity in dopamine D2 and other receptors involved in depression and/or cognition as a means of alleviating clinical depression or improving cognition.

6 Claims, No Drawings

(56) References Cited

OTHER PUBLICATIONS

Mucci, A. et al., "Levosulpiride: A Review of its Clinical Use in Psychiatry", Pharmacological Research vol. 31, No. 2, 1995, 95-101.
Green, B. et al., "Focus on Amisulpride", Current Medical Research and Opinions, vol. 18, No. 3, 2002, 113-117.
Nakazawa, T. et al., Biol. Pharm. Bull., 26(4): 474-80, 2003.
Peuskens, J. et al., "Amisulpride improves depressive symptoms in acute exacerbations of schizophrenia: comparison with haloperidol and risperidone" European Neuropsychopharmacology, 12 (2002), 305-10.
Schneier FR., et al., "Dopamine Transporters, D2 Receptors, and Dopamine Release in Generalized Social Anxiety Disorder", Depression and Anxiety, 26: 411-418, Epub Jan. 2009.
Noble E. P., "D2 Dopamine Receptor Gene in Psychiatric and Neurologic Disorders and its Phenotypes", Am J Medical Genetics Part B, Neuropsychiatr. Genet.116B:103-125, 2003.
Monti J.M. et al., "The involvement of dopamine in the modulation of sleep and waking", Sleep Medicine Reviews, 11, 113-133, Epub Feb. 2007.
Cools et al., Impulsive Personality Predicts Dopamine-Dependent Changes in Frontostriatal Activity during Component Processes of Working Memory, Journal of Neuroscience, May 16, 2007, 27(20): 5506-5514.
Cologno D. et al., High Prevalence of Dompaninergic Premonitory Symptoms in migraine patients with Restless Legs Syndrome: A pathogenetic link?, Neurol Sci.,(2008), 29:S166-168.
Ambrosini P.J., "A Pharmacological Paradigm for Urinary Incontinence and Enuresis", Journal of Clinical Psychopharmacology, Oct: 4(5): 247-53, 1984.
Palmiter R.D., "Is dopamine a physiologically relevant mediator of feeding behaviour", Trends in Neuroscience, vol. 30, No. 8: 375-381, 2007.
Capasso A., et al., Rev Recent Clin Trials, Jan:4(1): 63-9, 2009.
Wood P.B. et al., "Fibromyalgia patients show an abnormal dopamine response to pain", European Journal of Neuroscience, vol. 25, No. 12, 3576-3582, 2007.
Willner, P., International Clin. Psychopharm. 12 (Supplement 3):S7-S14, 1997.
Healy, E. et al., "Dopaminergic sensitivity and prediction of antidepressant response" Journal of Psychopharmacology, 14(2):152-156, 2000.
Samaha, A., et al., "Breakthrough dopamine supersensitivity during ongoing antipsychotic treatment leads to treatment failure over time", J. Neurosci. 27 (11): 2979-2986, 2007.
Shelton R.C., et al., "Augmentation of antidepressants with atypical antipsychotics for treatment-resistant major depressive disorder", Acta Psychiatr. Scand. 2008: 117:253-259.

* cited by examiner

COMPOSITIONS AND METHODS FOR ALLEVIATING DEPRESSION OR IMPROVING COGNITION

This application is a National Stage of International Application No. PCT/CA2009/000145, filed Feb. 5, 2009, which claims the benefit of Provisional Application No. 61/026,279, filed Feb. 5, 2008, the contents of both of which are herein incorporated by reference.

FIELD OF THE APPLICATION

The present application relates to compositions of receptor inhibitors, including dopamine receptor inhibitors such as haloperidol, and methods for alleviating clinical depression, improving cognition and/or alleviating depression-related symptoms in other conditions, diseases or syndromes. Furthermore, this application relates to methods of use of compositions of receptor inhibitors, including dopamine receptor inhibitors, to promote supersensitivity in receptor states associated with depression and/or cognition as a means of alleviating clinical depression, depression-related symptoms in other conditions, diseases and/or syndromes and improving cognition.

BACKGROUND OF THE APPLICATION

Depression and Antidepressants

Clinical depression is common, occurring in about one in five people during their lifetime and among the top four most common illnesses internationally as listed by the World Health Organization. The syndrome of depression may include persistent sadness, loss of self-esteem, difficulty concentrating, guilt, hopelessness, avoiding other people, loss of appetite, lack of enjoyment, and suicidal thoughts. Numerous conditions, diseases, and syndromes (e.g. anxiety disorders, post-traumatic stress, phobias, sleep disorders, fibromyalgia and other pain syndromes, migraine, enuresis, overactive bladder, anorexia and/or bulimia, obsessive-compulsive disorder, hair pulling, nail biting, teeth grinding etc.) exhibit symptoms of depression and are treated in part by anti-depressant agents. The following by way of example, is a brief summary of some of these disorders and current treatment modalities.

Post-Traumatic Stress Disorder

Post-traumatic stress disorder (PTSD) is an anxiety disorder that can develop following exposure to events that threaten or even cause physical harm. Some individuals experience a combination of both the threat of harm accompanied by physical harm. The response is an ongoing emotional reaction to the extreme psychological trauma caused by the stressors which overwhelm the individual's psychological defence mechanisms. Other terms for PSTS include railway spine, shell shock, battle fatigue, traumatic war neurosis or post-traumatic stress syndrome.

Events that may result in PTSD symptoms include assault, kidnapping, sexual assault, torture, prisoner of war, violent automobile accidents or receiving diagnosis of a life-threatening illness. Both children and adults experience PTSD. Children may experience this syndrome following sexually traumatic events such as age-inappropriate sexual experiences.

Typical symptoms include flashbacks and nightmares, avoidance of stimuli associated with the trauma, increased arousal such as difficulty falling or staying asleep, anger and hyper-vigilance. The symptoms unlike other types of syndromes persist, and may last more than six months resulting in significant impairment in social, family and work relationships.

Diagnostic criteria for PTSD are listed in Diagnostic and Statistical Manual of Mental Disorders IV and include the following: exposure to a traumatic event, persistent re-experience through nightmares or flashbacks, persistent avoidance of stimuli associated with the trauma including inability to discuss the event or other stimuli that may trigger flashbacks, persistent symptoms of increased arousal including difficulty sleeping, heightened anger and hyper-vigilance, symptoms lasting longer than one month, and impairment in social, work and relationships. Additionally, there are two criteria for a diagnosis of PTSD. The first requires that the person experienced, witnessed or confronted events involving actual or threatened serious injury or physical threat. The second is that the person's response involved intense fear, or helplessness.

Treatment typically involves various types of psychotherapy with some working better than others to reduce symptoms. Pharmacological strategies have reduced PTSD symptoms but have not been successful in eliminating them. These include antidepressants such as selective serotonin reuptake inhibitors (SSRI's) such as citalopram, escitalopram, fluvoxamine, paroxetine and sertraline, and tricyclic antidepressants (TCA's), which are associated with less efficacy and increased side-effects. Over-arousal symptoms may be alleviated using beta-blockers (e.g. propranolol), or alpha-adrenergic agonists (e.g. clonidine). These may block the effects of adrenaline on the amygdala. Other agents such as mood-stabilizers have been used including lithium, divalproex sodium, and carbamazepine and risperidone has been used to help with dissociation, mood and aggression. Some have tried combination therapies using a combination of psychotherapy (cognitive-behavioral therapy, group therapy, and exposure therapy are popular) and medications such as antidepressants, e.g. SSRI's, SNRI's (serotonin-norepinephrine reuptake inhibitors) such as venlafaxine, NaSSA's (noradrenergic and selective serotonergic uptake inhibitors) such as mirtazapine and tricyclic antidepressants such as amitriptyline or atypical antipsychotic drugs such as quetiapine and olanzapine.

Phobias

A phobia is generally described as an irrational and persistent fear of certain situations, activities, things, or people and occurs in about 8.7-18.1% of Americans (Kessler R C. et al., Arch. of Gen. Psych., 62; 617-27, 2005). If the fear is beyond one's control then one might be diagnosed with an anxiety disorder. Anxiety disorders such as social anxiety disorder, may be treated in part with the various antidepressant agents (e.g. escitalopram, fluvoxamine, paroxetine, sertraline, and venlafaxine) to relieve some symptoms; however, the efficacy is relatively low and there are associated-effects of the various agents (Hansen R A. et al., *Int Clin Psychopharmacol.* 23(3): 170-9.2008).

Fibromyalgia and other Pain Syndromes

Fibromyalgia (fibromyositis and fibrositis) is a chronic disease occurring in approximately 2% of the population and is characterized by ongoing pain throughout the body, sleeping disturbances, and chronic exhaustion. While fibromyalgia may affect children, teenagers and males, the majority of sufferers are women between the ages of 20 and 50. The cause of fibromyalgia is unknown. Its development can appear after a traumatic experience (accident, emotional trauma, overworking, hormonal changes, sexual or physical abuse during childhood, or viral disease.) The disease has historically been considered either a musculoskeletal disease or neuropsychiatric condition; however studies have shown abnormalities within the central nervous system affecting brain regions that may be linked both to clinical symptoms.

Fibromyalgia symptoms include a combination of the following: non-restorative sleep leading to a feeling of chronic exhaustion, gastrointestinal problems (digestive tract spasms, constipation, diarrhea), headaches, migraines, increasing symptoms during stressful times, tendency to feel depressed or anxious, feeling of swelling or numbness, lack of concentration and memory loss and fatigue and muscle weakness. Regarding the neurological effects, patients often experience cognitive dysfunction (known as "brain fog" or "fibrofog"), characterized inability to concentrate difficulties with short and long-term memory, short-term memory consolidation, impaired speed of performance, inability to multi-task, cognitive overload, diminished attention span, anxiety and depressive symptoms.

Although, fibromyalgia is associated with polymorphisms of genes in the serotoninergic, dopaminergic and catecholaminergic systems these polymorphisms are not specific for fibromyalgia.

There is a proposal that the central abnormality responsible for symptoms associated with fibromyalgia is a disruption of normal dopamine-related neurotransmission. Dopamine is best known for its role in the pathology of schizophrenia, Parkinson's disease and addiction. Dopamine is thought to play a role in restless leg syndrome, commonly seen in fibromyalgia patients as well as in pain perception and natural analgesia. Thus, a reduction in the dopamine transmission system may be involved in this disease.

A reduction in dopamine synthesis has been reported in fibromyalgia patients assessed by positron emission tomography (PET) which demonstrated a reduction in dopamine synthesis in several brain regions in which dopamine plays a role in inhibiting pain perception, including the mesencephalon, thalamus, insular cortex and anterior cingulate cortex (Wood et al., J. Neurosci. 27: 5506-5514, 2007). Another study demonstrated that, whereas healthy individuals release dopamine into the caudate nucleus and putamen during a tonic experimental pain stimulus (i.e. hypertonic saline infusion into a muscle bed) (Scott D J, et al. J. Neurosci. 26 (42): 10789-95, 2006), fibromyalgia patients fail to release dopamine in response to pain and, in some cases, actually have a reduction in dopamine levels during painful stimulation (Wood P B. et al. J. Neurosci. 25 (12): 3576-82, 2007). Moreover, a substantial subset of fibromyalgia patients respond well in controlled trials to pramipexole, a dopamine agonist that selectively stimulates dopamine D2/D3 receptors and is used to treat both Parkinson's disease and restless leg syndrome (Holman A J. et al. Arthritis Rheum. 52 (8): 2495-505, 2005).

The diagnosis of fibromyalgia is done through a combination of observations. These include: presence of generalized pain lasting more than three months (above and below the waste and on the left and right side of the body and on the front and back of the body and pain when pressure is applied to at least 11 of 18 tender points.

While there is no generally accepted cure for fibromyalgia, several treatments have reduced symptoms, including medications, patient education, exercise and behavioral interventions.

Pharmacological treatments include non-steroidal anti-inflammatory agents, anti-depressants including TCAs, SSRIs and SNRIs, anti-seizure medications (e.g. gabapentin, pregabalin), and dopamine agonists (e.g. pramipexole, ropinirole). While none of these agents are curative, many such as the TCAs have unwanted side effects.

Anorexia Nervosa

Anorexia Nervosa (AN) is characterized by extreme concern about body weight and shape, severe self-imposed weight loss, and endocrine dysfunction. Body weight in these individuals through voluntary starvation, purging, excessive exercise, or other diet control methods including diet pills or diuretic drugs. Primarily, adolescent females are affected; however, about 10% of individuals with the diagnosis are male. Anorexia nervosa, can involve neurobiological, psychological, and sociological components, and can lead to death in certain circumstances.

The diagnostic criteria include the ICD-1-diagnostic criteria and the DSM-IV-TR criteria. According to the DSM-IV-TR criteria a person diagnosed with anorexia must show the following types of traits: Refusal to maintain body weight at or above a minimally normal weight for age and height (e.g., weight loss leading to maintenance of body weight less than 85% of that expected; or failure to make expected weight gain during period of growth, leading to body weight less than 85% of that expected); intense fear of gaining weight or becoming obese; disturbance in the way in which one's body weight or shape is experienced, undue influence of body weight or shape on self-evaluation, or denial of the seriousness of the current low body weight; absence of at least three consecutive menstrual cycles (amenorrhea) in women who have had their first menstrual period but have not yet gone through menopause (postmenarcheal, premenopausal).

Treatments for anorexia involve behavioural therapy as well as pharmacological methods. Pharmacological methods have included SSRIs or other antidepressant medications but these have not been found to be generally effective for either treating anorexia (Claudino A M., et al. Cochrane Database Syst Rev, 1, CD004365, 2006) or preventing relapse (Walsh B T., et. al., AMA, 295(22), 2605-12, 2006).

Anorexia may be linked to a disturbed serotonin system, especially areas of the brain with $5HT_{1A}$ (Kaye W H, et al., Physiol Behav, 86(1-2), 15-7. 2005. This system is linked to anxiety, mood and impulse control. Other hypotheses involve modulation of the dopamine signaling pathway. For example, the hypothalamus is important in integrating various hormonal and neuronal signals to regulate appetite and metabolism and thereby serves in the homeostasis of body weight regulation. Additional neural circuits superimposed on this system have the potential to override the homeostatic signals, resulting in either gluttony or anorexia at the extremes. Midbrain dopamine neurons have long been implicated in mediating reward behavior and the motivational aspects of feeding behavior. Recent results reveal that hormones implicated in regulating the homeostatic system also impinge directly on dopamine neurons. For example, leptin and insulin directly inhibit dopamine neurons, whereas ghrelin activates them (Palmiter R D., Trends Neurosci. 30(8):375-81, 2007). Some have suggested an over active dopaminergic system may lead to hyperactivity associated with eating disorders and that antagonism to the system may improve conditions such as anorexia (Verhagen L A. et al., Eur Neuropsychopharmacol. Oct. 30[Epub ahead of print], 2008); however, to date significant strides have not been made in the treatment of these individuals.

As evident from this summary, there are numerous diseases, syndromes or conditions with depression-related symptoms that are treated with anti-depressant agents and many of these conditions have attributes that are related to changes in the dopaminergic system.

Types of Antidepressants and their Mechanisms of Action

There are many types of antidepressants used in clinical practice. The various types of antidepressant drugs can be grouped according to basic mechanisms of action, including the following:

1. Antidepressants that mainly inhibit neuronal reuptake of norepinephrine (noradrenaline) and to a lesser extent inhibit neuronal reuptake of dopamine and serotonin.
2. Antidepressants that inhibit the neuronal reuptake of serotonin (SSRI)
3. Antidepressants that inhibit the neuronal reuptake of dopamine.
4. Antidepressants that inhibit the neuronal reuptake of both norepinephrine and serotonin.
5. Antidepressants that inhibit the serotonin type-2 receptor.
6. Antidepressants that inhibit monoamine oxidase.
7. Antidepressants that stimulate adrenoceptors or dopamine receptors directly.
8. Mood stabilizers/preventatives.
9. Antipsychotics used for psychosis but which may treat the depression within the psychotic illness.
10. Vilazodone-type combined mechanism of SSRI and 5HT1A stimulation.

Based on the above mechanisms, antidepressants include a number of distinct classes of compounds acting at the level of the receptor. Selective serotonin reuptake inhibitors (SSRI's) are thought to prevent reuptake of serotonin by the presynaptic nerve, thus maintaining higher levels of 5-HT at the synapse. Examples of these agents include: fluoxetine (Prozac), paroxetine (Paxil), escitalopram (Lexapro, Esipram), citalopram (Celexa), and sertraline (Zoloft). Serotonin-norepinephrine reuptake inhibitors (SNRI's) have effects on both norepinephrine and 5-HT and include: venlafaxine (Effexor) and duloxetine (Cymbalta). Noradrenergic and specific serotonergic antidepressants are thought to increase norepinephrine and serotonin transmission by blocking pre-synaptic α-2 adrenergic receptors. One agent in this class is mirtazapine (Avanza, Zispin, Remeron). Norepinephrine reuptake inhibitors (NRI's) prevent reuptake of norepinephrine by presynaptic neurons and includes reboxetine (Edronax). Norepinephrine-dopamine reuptake inhibitors, including bupropion (Wellbutrin, Zyban), inhibit reuptake of norepinephrine and dopamine. Tricyclic antidepressants (TCA's) block the reuptake of norepinephrine and serotonin and include amitriptyline and desipramine. Monoamine oxidase inhibitors (MAOI's) block the enzyme, monoamine oxidase, which breaks down the neurotransmitters dopamine, serotonin, and norepinephrine (noradrenaline). An example includes phenelzine (Nardil).

Adverse Reactions Associated with Antidepressant Therapies

Currently-available drugs for treating depression have delayed onset of action, poor efficacy, anticholinergic effects at therapeutic doses, cardiotoxicity, convulsions and the clinical risk of overdosing. In particular, side effects of SSRI's include nausea, diarrhoea, headaches and sexual dysfunction such as loss of libido, failure to reach orgasm and erectile problems. Serotonin syndrome is also associated with the use of SSRI's. The Food and Drug Administration has included Black Box warnings on all SSRI's stating that they double the potential for suicide (from 2 in 1,000 to 4 in 1,000) in children and adolescents who are prescribed these drugs. Side effects of TCA's include dry mouth, blurred vision, drowsiness, dizziness, tremors, sexual problems, skin rash, and weight gain or loss. Side effects of MAOI's include some more uncommon but serious ones such as liver inflammation, heart attack, stroke, and seizures. MAOI's are of particular concern because there are potentially fatal interactions between this class of medication and certain foods (those containing tyramine). Furthermore, a large number of clinically depressed individuals remain refractory to currently-available therapies and the effects of therapies wane over time. These concerns point to the need for new, less adverse approaches to treat affective disorders such as depression.

Use of Antipsychotics for the Treatment of Depression

Although the use of antipsychotics for depression has been controversial (M. Robertson and M. R. Trimble, J. Affective Disorders 4: 173-193, 1982), amoxapine (Asendin®) and trazodone (Desyrel®) have been suggested to have effects on both types of illnesses, depression and psychosis (R. Apiquian et al., Schizophr. Res. 59: 35-39, 2003). Robertson and Trimble summarized studies showing that thioridazine, chlorpromazine, perphenazine, fluphenazine, thiothixene, flupenthixol, and chlorprothixene are as effective as imipramine, amitriptyline, or doxepin in treating depression, especially within the context of psychosis or schizophrenia. However, the doses of these antipsychotics are generally lower in treating depression, and it is likely that the antipsychotics are actually only removing the element of anxiety within the clinical depression as opposed to treating true clinical depression (M. M. Katz et al., Depression & Anxiety 4: 257-267, 1996-97).

More recently, reviews have summarized that low doses of the atypical antipsychotic amisulpride (50-100 mg/day) or levo-sulpiride (50-150 mg/day) are effective in dysythmia, a mild chronic form of depression, while higher doses (~100-400 mg/day) are effective against psychosis (L. Pani & G. L. Gessa, Mol. Psychiat. 7: 247-253, 2002; A. Mucci et al. Pharmacol. Res. 31: 95-101, 1995). However, amisulpride has not been approved for depression. Nor have these compounds been suggested for more severe forms of depression.

The antipsychotic doses of S-amisulpride and S-sulpiride are related to their dissociation constants at the dopamine D2 receptor, with that for S-amisulpride being 1.8 nM and that for S-sulpiride being 9.9 nM (P. Seeman. Canad. J. Psychiat. 47: 27-38, 2002). Amisulpride is a second-generation (atypical) antipsychotic, a substituted benzamide. It appears to be an effective agent in treating schizophrenia for what are characterized as positive and negative symptoms. The recommended doses are between 400 mg/day and 800 mg/day. Amisulpride demonstrates a good global safety profile, particularly when compared with first-generation antipsychotics, such as haloperidol. Studies point towards amisulpride's antidepressant effect in dysthymia and possibly treating affective psychosis and chronic fatigue syndrome (Green B. et al. Curr Med Res Opin. 18(3):113-7, 2002); however, the mechanism of this action is not established.

Haloperidol

As opposed to amisulpride, haloperidol is a first generation "typical" antipsychotic agent and has not been considered for treatment of depression or depression-type symptomology that occurs with other conditions, syndromes or diseases. Associated with this class of agents are many side-effects. Using the customary daily doses of 5 to 20 mg of oral haloperidol per day on a long-term basis, the following are such side effects. Cardiovascular effects include: tachycardia, hypotension, and hypertension, QT prolongation and/or ventricular arrhythmias, ECG patterns indicating torsade de pointes, and sudden and unexpected death. Central nervous system effects include extrapyramidal signs (EPS) such as Parkinson-like signs, akathisia or dystonia (including opisthotonos and oculogyric crises), tardive dyskinesia and tardive dystonia. The following are other central nervous system effects associated with the use of standard antipsychotic doses of haloperidol: insomnia, restlessness, anxiety, euphoria, agitation, drowsiness, depression, lethargy, headache, confusion, vertigo, and grand mal seizures. Neuroleptic malignant syndrome (NMS), hyperpyrexia and heat stroke have been reported with haloperidol.

The following is a current list of indications for the use of haloperidol: acute psychosis, such as drug-induced psychosis (LSD, amphetamines, phencyclidine), acute mania, hyperactivity, aggression, agitation and confusion associated with cerebral sclerosis, adjunctive treatment of alcohol and opioid withdrawal, treatment of neurological disorders such as tics, Tourette syndrome, and chorea, treatment of severe nausea/emesis (postoperative, side-effects of radiation and cancer chemotherapy), adjunctive treatment of severe chronic pain, always together with analgesics, personality disorders such as borderline personality disorders and in the treatment of intractable hiccups.

Animal Models of Depression

There are a limited number of animal models of depression (S. Kapur & J. J. Mann, Biol. Psychiat. 32: 1-17, 1992) and as with most animal models, their applicability to humans is in question. Nevertheless, there are four types of such models which have been used in the development of antidepressant agents.

1. The "learned helplessness" model, where animals are exposed to inescapable stressors such as to decrease spontaneous activity and decrease the effort to escape, effects which are reversed by imipramine, desipramine, amitryptiline, doxepin, iprindole, mianserin, iproniazid and pargyline or by electroshock (A. D. Sherman et al., Pharmacol. Biochem. Behav. 16: 449-454, 1982).

2. The "forced swim test" or "behavioral despair" is where rats are forced to swim in a limited space. After some hopeless attempts at escape, the rats become immobile, an effect which some antidepressants may reverse.

The relevance of these two animal "frustration" models to clinical depression has been questioned (P. Willner, Psychopharmacology 83: 1-16, 1984).

3. There are many types of rat behavior tests for motivation and reward. Although dopamine release is central to these behaviors, and antidepressants may have effects on such tests, the clinical relevance of such tests to human depression has been questioned (Refs. In S. Kapur & J. J. Mann, Biol. Psychiat. 32: 1-17, 1992).

4. While not a behavioral test, a consistent and reliable index of antidepressant action is the reduction in the density of beta-adrenoceptors in the rat cortex after 10 days or two weeks of antidepressant treatment, with the single exception of serotonin-selective uptake inhibitors. This effect holds not only for the various classes of antidepressants listed above, but also for other types of antidepressant treatment, such as nitric oxide synthase inhibitors (B. Karolewicz et al., Eur. J. Pharmacol. 215-220, 1999).

Role of Dopamine in Depression is shown by Antipsychotic Block of Antidepressants The following study is one example indicating a role for dopamine in depression. Using the behavioral despair test (forced swimming test) in mice, it was shown that apigenin significantly decreased the duration of immobility in the forced swimming test in mice, an indicator of an antidepressant effect. The authors showed that apigenin attenuated the forced swim test-induced decrease of DA turnover in the amygdala and increase of DA turnover in the hypothalamus. A relatively high dose of haloperidol (0.2 mg/kg), a dopamine D2 receptor antagonist, blocked the apigenin-induced decrease in immobility in the forced swimming test. These results suggested that the antidepressant properties of apigenin may involve dopamine (T. Nakazawa et al. Biol. Pharm. Bull., 26(4):474-80, 2003).

Antipsychotic agents differ in their efficacy on depression, depending on the clinical features and the drug dosage used. For example, one study examined the ability of various antipsychotics to treat the depressive symptoms in acute exacerbations of schizophrenia. As noted above, these effects may indicate a drug effect on reducing anxiety, rather than clinical depression. However, the finding suggested that there is a differential effect of various antipsychotic agents on these depressive symptoms. For example, amisulpride was better than haloperidol. The Brief Psychiatric Rating Scale (BPRS) anxiety/depression subscore found amisulpride (400-800 mg/day)(5.6±6.1) to be significantly better (P=0.011) than haloperidol (15-20 mg/day) (4.4±5.5) or risperidone (8 mg/day)(3.7±4.7). (J. Peuskens et al. *Eur Neuropsychopharmacol.*, 12(4):305-10, 2002).

These data suggest that not all antipsychotics or doses will be useful for inhibiting depressive symptoms. Moreover, the depression component in schizophrenia patients, exemplified above, may respond differently than endogenous depression that is not associated with schizophrenia or psychosis.

In addition, it is known that there are fundamental differences between antipsychotics based on their differing affinities for the dopamine D2 receptor. For example, traditional antipsychotics such as haloperidol and chlorpromazine bind tightly to the dopamine D2 receptor (P. Seeman et al., Am J. Psychiatry. 156:876-884, 1999), while the newer or atypical antipsychotic agents such as quetiapine, clozapine and amisulpride rapidly dissociate from the D2 receptor (P. Seeman et al., Can. J. Psychiatry 47:27-38, 1995).

A review of atypical antipsychotics for enhancing antidepressant action in major depression revealed that while small clinical studies appeared to show some improvement, large well-controlled clinical studies failed to show effectiveness of atypical antipsychotics in reducing major depressive disorder when used with antidepressant agents (Shelton R C et al. Acta. Psychiatr. Scand. (Jan 8 epub ahead of print, 2008).

Role of Dopamine in Cognition

It is known that there is a vast array of medications alleged to improve cognition. Such compounds include, for example, the following: modafinil (R. E. Morgan et al., Pharmacol. Biochem. Behav. 86: 531-541, 2007), rimonabant, donepezil (L. Wise et al., Neuropsychopharmacol. 32:1805-1812, 2007), various herbs (D. Kennedy, A. Scholey, Curr. Pharm. Des. 12: 4613-4623, 2006), nicotinic partial agonists (G. Dunbar et al., J. Clin. Pharmacol. 46: 715-726, 2006), memantine (D. R. Guay, Consult. Pharm. 18: 625-634, 2003), Ginkgo biloba (M. Zhang, J. Cai, Behav. Pharmacol. 16: 651-656, 2005), Norepinephrine uptake inhibitor (atomoxetine) (E. Tzavara et al., Mol. Psych. 11:187-195, 2006), D2 receptor agonist bromocriptine (R. Cools et al., J. Neurosci. 27: 5506-5514, 2007), cycloserine (J. E. Bailey et al., Psychopharmacology 193: 579-585, 2007), ampakines (Cortex pharmaceuticals), and caffeine.

There are many components to cognition, including overall long-term memory, working memory, performance ability, motivation, alertness, mood, attention and distractibility, to mention just a few. While each of the compounds and medications listed above may improve one or two of the components of cognition, there is no single compound that improves all aspects and components of cognition.

Moreover, each of these compounds has adverse effects. For example, nicotinic agonists elicit dizziness, headache, and many other somatic signs and symptoms, while memantine can cause depression, insomnia, akathisia, agitation, dizziness, drowsiness, restlessness and hyper-excitability (D. R. Guay, Consult. Pharm. 18: 625-634, 2003).

Of the many components constituting the overall cognitive process, the features of attention, motivation and mood are central. That is, an individual who is not motivated, not attentive, and in a depressed mood, would not score high on any scale of cognition.

Role of Dopamine in other Diseases, Syndromes or Conditions

It should be noted that a role for dopamine has been shown for other diseases, syndromes or conditions which have typically been treated with anti-depressant agents including anxiety disorders (Schreier F R., et al. Depress Anxiety. Epub Jan. 2009), post-traumatic stress (Noble E P., Am J Med Genet B Neuropsychiatr Genet. 1;116B(1):103-25; 2003), sleep (Monti J M., *Sleep Med Rev*. Apr;11(2):113-33. Epub Feb, 2007), fibromyalgia and other pain syndromes (Wood et al., J. Neurosci. 27: 5506-5514, 2007), migraine (Cologno D. et al., *Neurol Sci.*, May;29 Suppl 1:S166-8, 2008), enuresis and urinary incontinence (Ambrosini P J., J Clin Psychopharmacol. Oct;4(5):247-53, 1984), anorexia (Palmiter R D., Trends Neurosci. 30(8):375-81, 2007) and bulimia (Capasso A., et al. Rev Recent Clin Trials. Jan;4(1):63-9, 2009).

SUMMARY OF THE APPLICATION

Due to the relatively high number of adverse reactions associated with the currently approved antidepressants, the fact that a large number of clinically depressed individuals remain refractory to currently available therapies, and that the effects of therapies wane over time, there is a need for new approaches to treat clinical depression. Furthermore, there is a need for new approaches to treat depression-associated symptoms of other conditions, syndromes or diseases for which anti-depression agents are sometimes used. Described herein are novel compositions and methods for the treatment of clinical depression, cognition and/or other conditions, syndromes or diseases for which anti-depressant agents are prescribed, which are expected to result in improved efficacy and more ready acceptance by depressed patients or individuals with diminished cognition. The present application is based on the principle that a low level of post-synaptic receptor supersensitivity, as controlled by the level of receptors in the functional or "high affinity" state, can simultaneously mediate the two processes of antidepressant and pro-cognitive action.

The present application includes a method of treating depression, of improving cognition, and/or treating other conditions, syndromes or diseases for which anti-depressant agents are prescribed comprising administering, to a subject in need thereof, an amount of a receptor inhibitor that is effective to elevate amounts of the high affinity state of the receptor, inducing receptor supersensitivity, wherein the receptor state is associated with depression, cognition and/or other conditions, syndromes or diseases for which anti-depressant agents are prescribed.

In a further aspect, the method also includes stopping administration of the receptor inhibitor after receptor supersensitivity is induced, followed by restarting administration of the receptor inhibitor after a time sufficient for receptor supersensitivity to decrease and, optionally, repeating the stopping and restarting administration cycle for a period of time effective to treat the depression, to improve cognition and/or to treat other conditions, syndromes or diseases for which anti-depressant agents are prescribed.

The present application further includes a use of a receptor inhibitor to treat depression, to improve cognition and/or to treat other conditions, syndromes or diseases for which anti-depressant agents are prescribed, wherein said receptor inhibitor is used in an amount and for a time period that is effective to elevate amounts of the high affinity state of the receptor, inducing receptor supersensitivitity, wherein the receptor state is associated with depression, cognition and/or other conditions, syndromes or diseases for which anti-depressant agents are prescribed. In an embodiment, the use of the receptor inhibitor is stopped after receptor supersensitivity is induced, followed by restarting use of the receptor inhibitor after a time sufficient for receptor supersensitivity to decrease and, optionally, repeating the stopping and restarting cycle for a period of time effective to treat the depression, cognition and/or other conditions, syndromes or diseases for which anti-depressant agents are prescribed.

In an embodiment more than one receptor inhibitor is used, each acting on the same or on different receptors associated with depression, cognition and/or other conditions, syndromes or diseases for which anti-depressant agents are prescribed.

In an embodiment of the application the receptor associated with depression, cognition and/or other conditions, syndromes or diseases for which anti-depressant agents are prescribed is the dopamine D2 receptor.

In an embodiment of the application, the amount of a dopamine D2 receptor inhibitor that is effective to elevate dopamine $D2^{High}$ receptor amounts, thereby inducing dopamine supersensitivity, is between approximately 1-10% or between 11-30% of a typical daily antipsychotic dose of the dopamine D2 receptor inhibitor.

The low dosage of dopamine D2 receptor inhibitor, which avoids any Parkinsonism or extrapyramidal motor reactions, optionally in combination with the intermittent dosing, is a unique design that results in dopamine D2 receptor supersensitivity. The dopamine supersensitivity is mediated by the dopamine D2 receptor inhibitor induction of an increase in the proportion of dopamine D2 receptors that are in the high-affinity state, or $D2^{High}$. The method of the present application is applicable to haloperidol and other antipsychotic agents and other receptors associated with depression, cognition and/or other conditions, syndromes or diseases for which anti-depressant agents are prescribed.

In an embodiment of the application, the other conditions, syndromes or diseases for which anti-depressant agents are prescribed include, but not limited to, anxiety disorders, post-traumatic stress, phobias, sleep disorders, movement disorders, fibromyalgia and other pain syndromes, chronic fatigue syndrome, migraine, enuresis, overactive bladder, anorexia and/or bulimia, obsessive-compulsive disorder, hair pulling, nail biting and teeth grinding, whose symptoms are treated using standard antidepressant agents.

Other features and advantages of the present application will become apparent from the following detailed description. It should be understood, however, that the detailed description and the specific examples while indicating preferred embodiments of the application are given by way of illustration only, since various changes and modifications within the spirit and scope of the application will become apparent to those skilled in the art from this detailed description.

DETAILED DESCRIPTION OF THE APPLICATION

The present application describes the antidepressant or pro-cognitive action of a low dose of haloperidol or another antipsychotic agent which is based on its ability to elevate the proportion of dopamine D2 receptors that are in the high-affinity state. This results in increased psychomotor activity and antidepressant and pro-cognitive actions. This result is extended to other receptor inhibitors that are able to elevate the proportion of those receptors that are in the high-affinity state.

It is known that individuals with clinical depression release abnormally low amounts of norepinephrine and dopamine (G. Lambert et al., Arch. Gen. Psychiat. 57: 787-793, 2000). Although high doses of haloperidol readily increase the release of dopamine in various regions of the brain in animals and humans, this increased release is not effective in alleviating depression because the high doses block most of the dopamine D2 receptors (T. Zetterstrom et al., Eur. J. Pharmacol. 106: 27-37, 1984; B. H. C. Westerink et al., Eur. J. Pharmacol. 361: 27-33, 1998; R. Davila et al., Arch. Gen. Psychiat. 45: 564-567, 1988; I. Elman et al., Neuropsychopharmacology 27: 293-300, 2002).

Antidepressant agents are also used to treat or modify the depressive symptoms of other syndromes, conditions or diseases.

By way of explanation and not limitation, a description follows explaining the relationship of dopamine and dopamine receptors and the pain experienced by patients with fibromyalgia. One of the characteristics of fibromyalgia is chronic widespread pain and bodily tenderness which are often accompanied by affective disturbances. There is increasing evidence suggesting that fibromyalgia may involve a dysfunction of brain modulatory systems. While brain dopamine is best known for its role in pleasure, motivation and motor control, dopamine also appears to be involved in pain modulation. Because dopamine is implicated in both pain modulation and affective processing, it has been hypothesized that fibromyalgia may involve a disturbance of dopaminergic neurotransmission (Wood P B. et al., *Eur J Neurosci.*, 25(12): 3576-82, 2007). In the study conducted by Wood et al., fibromyalgia patients and matched healthy control subjects were subjected to deep muscle pain produced by injection of hypertonic saline into the anterior tibialis muscle. PET was used to determine the endogenous release of dopamine in response to painful stimulation, whereby the binding of [(11)C]-raclopride (D2/D3 ligand) was measured in the brain during injection of painful hypertonic saline and nonpainful normal saline. From a behavioral perspective, fibromyalgia patients experienced the hypertonic saline as more painful than healthy control subjects. Control subjects released dopamine in the basal ganglia during the painful stimulation, whereas fibromyalgia patients did not. In control subjects, the amount of dopamine release correlated with the amount of perceived pain but in fibromyalgia patients no such correlation was observed. This is the first direct evidence that fibromyalgia patients have an abnormal dopamine response to pain. The disrupted dopaminergic reactivity in fibromyalgia patients could be a critical factor underlying the widespread pain and discomfort in fibromyalgia. Typically anti-depressant agents are prescribed to reduce the depressive symptoms of the chronic pain. Here, however, the authors suggested treatment with dopaminergic agents in an attempt to increase the presynaptic dopamine levels to improve pain reaction. While this may show some benefit in the short-term, is is submitted that this treatment will, over time, have similar issues to other such drugs including various toxicities, waning improvement in drug effectiveness, etc. The present application provides a solution to these issues through methods and compositions to increase the sensitivity of the dopamine receptors to endogenous dopamine so that even though a reduced amount of dopamine may be released in response to pain, the dopamine will stimulate the sensitized dopamine receptors normalizing the response to pain.

The dopamine D2 receptor has also been implicated in post-traumatic stress disorder, movement disorders and migraine. In fact, phenotypic differences in humans with various such disorders have been associated with dopamine D2 variants. These include reduced D2 dopamine receptor numbers in brains of subjects who carry the dopamine D2 A1 allele (Noble E P., *Am J Med Genet B Neuropsychiatr Genet.* 1;116B(1):103-25; 2003). The present application provides a solution to these issues through methods and compositions to increase the sensitivity of the dopamine receptors to endogenous dopamine so that even though there may be a reduced number of dopamine receptors or reduced dopamine released in response to stimuli, the dopamine will stimulate the sensitized dopamine receptors effectively normalizing the dopamine response.

It has been shown that treatment with antidepressant drugs (at normal antidepressant doses) produces a sensitization of behavioural responses to agonists acting at dopamine D2 receptors (so-called dopamine supersensitivity, Willner, P. International Clin. Psychopharm. 12 (Supplement 3):S7-S14, 1997; Healy, E. et al. J. Psychopharm. 14:152-156, 2000; C. Spyraki and H. C. Fibiger, Eur. J. Pharmacol. 74: 195-206, 1981; S. Kapur and J. J. Mann, Biol. Psychiatry 32: 1-17, 1992). Such a sensitizing action presumably assists in eliciting the clinical antidepressant and pro-cognitive actions; however, these effects are accompanied by numerous side-effects.

It has been found that all antipsychotic drugs block dopamine D2 receptors in direct relation to their antipsychotic clinical potency (P. Seeman et al., PNAS, 1975).

The present application relates to novel and heretofore undisclosed compositions and methods to produce controlled receptor supersensitivity with unusually low toxicity for the treatment of depression, in the improvement of cognition, and/or in the treatment or modification of the depressive symptoms of other syndromes, conditions or diseases.

The present application includes a method of treating depression, of improving cognition and/or treating other syndromes, conditions or diseases for which anti-depressant agents are prescribed, comprising administering, to a subject in need thereof, an amount of a receptor inhibitor that is effective to elevate amounts of the high affinity state of the receptor, inducing receptor supersensitivity, wherein the receptor state is associated with depression, cognition, and/or other syndromes, conditions or diseases for which anti-depressant agents are prescribed.

In a further aspect, the method also includes stopping administration of the receptor inhibitor after receptor supersensitivity is induced, followed by restarting administration of the receptor inhibitor after a time sufficient for receptor supersensitivity to decrease and, optionally, repeating the stopping and restarting administration cycle for a period of time effective to treat the depression, to improve cognition and/or treatment of other syndromes, conditions or diseases for which anti-depressant agents are prescribed.

The present application further includes a use of a receptor inhibitor to treat depression, to improve cognition, and/or to treat other syndromes, conditions or diseases for which anti-depressant agents are prescribed wherein said receptor inhibitor is used in an amount and for a time period that is effective to elevate amounts of the high affinity state of the receptor, inducing receptor supersensitivity. In an embodiment, the use of the receptor inhibitor is stopped after receptor supersensitivity is induced, followed by restarting use of the receptor inhibitor after a time sufficient for receptor supersensitivity to decrease and, optionally, repeating the stopping and restarting cycle for a period of time effective to treat the depression, to improve cognition and/or to treat other syndromes, conditions or diseases for which anti-depressant agents are prescribed.

While one aspect of this application includes use of compositions of a dopamine D2 receptor inhibitor, including but not limited to haloperidol, which act on the dopamine D2 receptor, another aspect of the application includes the use of other agents which affect one or more other receptors associated with depression, cognition, and/or other syndromes, conditions or diseases for which anti-depressant agents are prescribed, including, for example, the serotonin receptor and central adrenergic receptors, and combinations thereof. This aspect of the application thus includes compositions and methods which result in controlled supersensitization of one or more of these receptors for the treatment of clinical depression, the improvement of cognition and/or the treatment of other syndromes, conditions or diseases for which anti-depressant agents are prescribed.

In an embodiment of the application, the other syndromes, conditions or diseases for which anti-depressant agents are prescribed, include, but are not limited to, anxiety disorders, post-traumatic stress, phobias, sleep disorders, movement disorders, fibromyalgia and other pain syndromes, chronic fatigue syndrome, migraine, enuresis, overactive bladder, anorexia and/or bulimia, obsessive-compulsive disorder, hair pulling, nail biting and teeth grinding. In a further embodiment, in these other syndromes, conditions or diseases, the method of the present application treats the depressive symptoms associated therewith.

In a further embodiment of the application, the methods and uses described herein are for treating depression and/or for improving cognition.

Compounds that induce receptor supersensitivity are also known in the art. To "induce receptor supersensitivity" refers to compounds that can produce an increased number or elevated density or amount of receptors in the high affinity state in a subject's brain, in particular compared to control levels.

By "increase" it is meant any detectable elevation in a variable, for example amount of receptors in the high affinity state in a subject's brain or receptor supersensitivity, for example compared to control levels.

By "decrease" it is meant any detectable reduction in a variable, for example amount of receptors in the high affinity state, or receptor supersensitivity, for example compared to controls.

In an embodiment of the present application, the dopamine D2 receptor inhibitor used to stimulate supersensitivity in the dopamine D2 receptor is an antipsychotic agent including, but not limited to, typical antipsychotic agents selected from haloperidol, chlorpromazine, fluphenazine, molindone, thiothixene, thioridazine, trifluoperazine, loxapine, perphenazine, prochlorperazine, pimozide, and zuclopenthixol and atypical antipsychotics selected from: aripiprazole (Abilify), clozapine (Clozaril), olanzapine (Zyprexa), olanzapine/fluoxetine (Symbyax), quetiapine (Seroquel), risperidone (Risperdal) and ziprasidone (Geodon). In a further embodiment, the dopamine D2 receptor inhibitor is haloperidol.

In a further embodiment of the present application the amount of a dopamine D2 receptor inhibitor that is effective to elevate dopamine $D2^{High}$ receptor amounts, inducing dopamine supersensitivity, are those amounts or doses which result in dopamine D2 supersensitivity and/or increased anti-depressant or pro-cognitive effect as shown in an animal model of depression or in humans using depression score systems, for example, the Hamilton depression scale (Hedlung and Vieweg, Journal of Operational Psychiatry, 1979, 10:149-165) or tests of memory. While it is understood that dopamine D2 receptor inhibitors have different potencies and dose should be adjusted according to the potency, it is an embodiment of the application that doses are approximately 1-10% or 11-30% of the typical daily antipsychotic dose of the agent. In another embodiment of the application, oral preparations of low-dose haloperidol for example, may be formulated, suitably as tablets, capsules, or drops, containing 0.05-2 milligrams, suitably 0.1-0.5 milligrams, or more suitably 0.2, 0.3 or 0.4 milligrams of haloperidol, per dosage unit. In another embodiment, the compounds described herein are administered initially in a suitable dosage that may be adjusted as required, depending on the clinical response.

In another embodiment of the present application, dose scheduling to be used to result in receptor supersensitivity and/or a reduction in depression and/or an increase in pro-cognitive action are to be determined as those schedules which in combination with appropriate dose results in receptor supersensitivity and/or increased antidepressant and/or pro-cognitive effect as shown in an animal model of depression or in humans using typical depression score systems. Dose schedules are expected to be altered according to the specific receptor inhibitors used to maximize the antidepressant and/or procognitive effects. As noted above, and in a further embodiment, the administration or use of the receptor inhibitor is stopped after receptor supersensitivity is induced, followed by restarting administration of the receptor inhibitor after a time sufficient for the induction of receptor supersensitivity to decrease and, optionally, repeating the stopping and restarting administration cycle for a period of time effective to treat the depression, to improve cognition and/or to treat the depressive symptoms of other syndromes, conditions or diseases. Examples of dose schedules include, but not limited to: between 1-10 days dosing with receptor inhibitor followed by between 1-10 days of dosing with placebo, between 6-10 days dosing with receptor inhibitor, followed by between 6-10 days of dosing with placebo or 7, 8 or 9 days dosing with receptor inhibitor, followed by 7, 8 or 9 days of dosing with placebo. Optionally the dosing of inhibitors and placebo is repeated for a period of time effective to treat depression, improve cognition and/or to treat other conditions syndromes or diseases for which antidepressants are prescribed. Another example of a dose schedule is the following: active receptor inhibitor taken 3 times per week (Monday, Wednesday and Friday) followed by placebo on alternate days including the weekends. The duration of receptor inhibitor schedules can be adjusted to ensure a sustained reduction in depression or an enhanced cognitive action by one skilled in the art.

In a further embodiment, the amount of receptor inhibitor that is administered is gradually increased, or graded, during the dosing time period. The graded doses are to avoid any possible minor side-effects or to allow the individual to become accustomed to any minor side-effects such as headache, in the unlikely event that such minor side-effects occur. Modest progressive increments of amounts of receptor inhibitor over the dosing time period is based on the principle that dopamine supersensitivity can break through before the treatment is completed. Such breakthrough dopamine supersensitivity is known to occur in animals given higher doses of haloperidol (Samaha, A.-N., Seeman, P., Stewart, J., Rajabi, H., Kapur, S.: "Breakthrough" dopamine supersensitivity during ongoing antipsychotic treatment leads to treatment failure over time. J. Neurosci. 27 (11): 2979-2986 [2007]). While breakthrough dopamine supersensitivity is welcome during the treatment, it is considered better to complete and consolidate the supersensitivity rather than stop the treatment before the treatment cycle is completed.

In another embodiment of the present application the receptor occupancy after administering or using the amount of a receptor inhibitor that is effective to elevate receptor$^{High}$ amounts, inducing receptor supersensitivity, is on the order of 2%-10%. Other examples of receptor occupancy that are included in this application are 11%-15% and 16%-20% and 20% to 25%. In another embodiment, the degree of receptor binding required to initiate a reduction in depression, an improvement in cognition and/or an improvement in depressive symptoms of other syndromes, conditions or diseases varies with the receptor inhibitor.

These combinations of low doses of receptor inhibitor agent and novel dose-schedules result in sustained supersensitivity associated with increasing the proportion of receptors in the high-affinity state. This sustained increase in the proportion of receptors in the high-affinity state results in antidepressant activity, improved cognition and/or improvement in the depressive symptoms of other syndromes, conditions or diseases. In fact, work (P. Seeman, Unpublished Results) has shown that many of the commonly used antidepressants (e.g., fluoxetine, imipramine) cause dopamine behavioral supersensitivity in animals, while at the same behavioral dopamine supersensitivity is associated with elevated $D2^{High}$ receptors. Furthermore, in animals, an increase in dopamine $D2^{High}$ leads to modest hyperactivity (P. Seeman et al., PNAS Mar. 1, 2005), one of the indicators of an antidepressant effect as discussed in the animal models described above.

Low dose haloperidol and low doses of other antipsychotics have not been used clinically as antidepressants or pro-cognitive compounds.

As used herein, the term "cognition" refers to any process related to learning acquisition, memory consolidation and retrieval.

As used herein, the term "depression" refers to "clinical depression" or "major depressive disorder".

As used herein the term "receptor supersensitivity" refers to a state of a receptor that leads to an enhanced response upon stimulation by a lower dose or amount of an agonist than the corresponding control. A receptor which is linked to a G protein (of which there are many types) can exist in two states. One state has a high affinity for the natural receptor agonist, and this state is referred to as the high-affinity state. The other state has a low affinity for the natural receptor agonist and this state is referred to as the low-affinity state. As an example, dopamine, the natural receptor agonist for the D2 receptor has a dissociation constant of 1.5 nM for the high affinity state, or $D2^{High}$ and a dissociation constant of approximately 200-2000 nM for the low-affinity state, or $D2^{Low}$. Depending on local conditions in vitro or in vivo, the two states can quickly convert into each other. Because the high-affinity state is considered the functional state (S. R. George et al., Endocrinology 117: 690, 1985), the process of "desensitization" occurs whenever the high-affinity state converts into the low-affinity state.

That low dose haloperidol is an effective antidepressant or cognitive enhancer in animals is at least in part related to its elevation of $D2^{High}$ receptors, and, in an embodiment of this application, is effective in clinical depression, diminished cognition and/or improvement of the depressive symptoms of other syndromes, conditions or diseases. Although the commonly used antipsychotic dosage of haloperidol is between 5 and 20 mg per day (oral dose), the present method advocates an antidepressant pro-cognitive dose of 0.05 mg to 0.5 mg (oral) given either each day for about 3 to about 10 days, suitably 5 to 7 days. In an embodiment, the dosage is either maintained or stopped for a week and re-started one or two weeks later, depending on the clinical state of the patient. In another embodiment, the amount of haloperidol is gradually increased during the treatment period. For example, a seven-day regimen of low-dose haloperidol to alleviate depression by means of gradually inducing dopamine supersensitivity is done by administering oral haloperidol as follows: 0.2 mg on day 1, 0.2 mg on day 2, 0.25 mg on day 3, 0.25 mg on day 4, 0.25 mg on day 5, 0.3 mg on day 6 and 0.3 mg on day 7, followed by a complete cessation of the medication until a repeat treatment may be clinically indicated. In another embodiment the dose of haloperidol is maintained during the treatment period. For example, a seven-day regimen of low-dose haloperidol to alleviate depression by means of inducing dopamine supersensitivity is done by administering oral haloperidol as follows: 0.25 mg once daily for 7 days, followed by a complete cessation of the medication until a repeat treatment may be clinically indicated. In yet another embodiment of the application the amount of drug administered per day is determined taking into account the body mass index ensuring that the dose is sufficient to induce supersensitivity. In another embodiment of the application, the dosage forms may be administered from a blister pack where the patient takes one dose daily and where a series of the doses are of active ingredient and another series of doses are placebo. This embodiment allows the patient to take one dose per day to maintain a steady dosing regimen and allows the physician to establish how many active doses are required, followed by placebo doses to ensure maintenance of supersensitibity. It should be noted that for any of the embodiments the dosage and dose interval can be adjusted to provide an antidepressant effect or a reduction in depressant-associated symptoms. These doses and dosing regimens are by way of example and not limitation.

The receptor inhibitors, including haloperidol may be used in any pharmaceutically acceptable form, including salts, solvates and prodrugs thereof.

The term "pharmaceutically acceptable" means compatible with the treatment of animals, in particular, humans.

The term "pharmaceutically acceptable salt" means an acid addition salt or a basic addition salt which is suitable for or compatible with the treatment of patients.

The term "pharmaceutically acceptable acid addition salt" as used herein means any non-toxic organic or inorganic salt of any base compound. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, acid addition salts are more soluble in water and various hydrophilic organic solvents, and generally demonstrate higher melting points in comparison to their free base forms. The selection of the appropriate salt will be known to one skilled in the art.

The term "pharmaceutically acceptable basic addition salt" as used herein means any non-toxic organic or inorganic base addition salt of any acid compound. Illustrative inorganic bases which form suitable salts include lithium, sodium, potassium, calcium, magnesium or barium hydroxide. Illustrative organic bases which form suitable salts include aliphatic, alicyclic or aromatic organic amines such as methylamine, trimethylamine and picoline, alkylammonias or ammonia. The selection of the appropriate salt will be known to a person skilled in the art.

The formation of a desired compound salt is achieved using standard techniques. For example, the neutral compound is treated with an acid or base in a suitable solvent and the formed salt is isolated by filtration, extraction or any other suitable method.

The term "solvate" as used herein means a compound, or a pharmaceutically acceptable salt of a compound, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate". The formation of solvates of the compounds will vary depending on the compound and the solvate. In general, solvates are formed by dissolving the compound in the appropriate solvent and isolating the solvate by cooling or using an antisolvent. The solvate is typically dried or azeotroped under ambient conditions.

The present application includes within its scope, prodrugs of the receptor inhibitors. In general, such prodrugs will be functional derivatives of a compound which are readily convertible in vivo into the compound from which it is notionally derived. Prodrugs may be conventional esters formed with available hydroxy, or amino group. For example, an available OH or NH group in a compound may be acylated using an activated acid in the presence of a base, and optionally, in inert solvent (e.g. an acid chloride in pyridine). Some common esters which have been utilized as prodrugs are phenyl esters, aliphatic ($C_8$-$C_{24}$) esters, acyloxymethyl esters, carbamates and amino acid esters. In further embodiments, the prodrugs are those in which one or more of the hydroxy groups in the compounds is masked as groups which can be converted to hydroxy groups in vivo. Conventional procedures for the selection and preparation of suitable prodrugs are described, for example, in "Design of Prodrugs" ed. H. Bundgaard, Elsevier, 1985.

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

Whether or not a giver therapy is effecting "treatment" of a disease, condition or syndrome can be determined using standard assays known in the art. For example, the Hamilton Depression Scale (Hedlung and Vieweg, Journal of Operational Psychiatry, 1979, 10:149-165), assays for reduced pain sensation and tests for memory.

"Palliating" a disease or disorder means that the extent and/or undesirable clinical manifestations of a disorder or a disease state are lessened and/or time course of the progression is slowed or lengthened, as compared to not treating the disorder.

The term "prevention" or "prophylaxis", or synonym thereto, as used herein refers to a reduction in the risk or probability of a patient becoming afflicted with depression, diminished cognition and/or with the depressive symptoms of other syndromes, conditions or diseases.

The term "subject" or "patient" or synonym thereto, as used herein includes all members of the animal kingdom, especially mammals, including human. The subject or patient is suitably a human.

The receptor inhibitor is suitably formulated into pharmaceutical compositions for administration to human subjects in a biologically compatible form suitable for administration in vivo.

The compositions described herein can be prepared by known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

In accordance with the methods of the use application, the described compounds, salts or solvates thereof may be administered to a patient in a variety of forms depending on the selected route of administration, as will be understood by those skilled in the art. The compositions of the application may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time.

Compounds described herein may be orally administered, for example, with an inert diluent or with an assimilable edible carrier, or may be enclosed in hard or soft shell gelatin capsules, or may be compressed into tablets, or may be incorporated directly with the food of the diet. For oral therapeutic administration, the compounds may be incorporated with excipient and used in the form of ingestible tablets, buccal tablets, troches, capsules, elixirs, suspensions, syrups, wafers, and the like.

Compounds described herein may also be administered parenterally. Solutions can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. Conventional procedures and ingredients for the selection and preparation of suitable formulations are described, for example, in Remington's Pharmaceutical Sciences (1990-18th edition) and in The United States Pharmacopeia: The National Formulary (USP 24 NF19) published in 1999.

The pharmaceutical forms suitable for injectable use include sterile aqueous solutions or dispersion and sterile powders for the extemporaneous preparation of sterile injectable solutions or dispersions. In all cases the form must be sterile and must be fluid to the extent that easy syringability exists. Ampoules are convenient unit dosages.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

Compositions for topical administration may include, for example, propylene glycol, isopropyl alcohol, mineral oil and glycerin. Preparations suitable for topical administration include liquid or semi-liquid preparations such as liniments, lotions, applicants, oil-in-water or water-in-oil emulsions such as creams, ointments or pastes; or solutions or suspensions such as drops; or solid controlled release forms such as transdermal patches. In addition to the aforementioned ingredients, the topical preparations may include one or more additional ingredients such as diluents, buffers, flavouring agents, binders, surface active agents, thickeners, lubricants, preservatives, e.g. methyl hydroxybenzoate (including antioxidants), emulsifying agents and the like.

Sustained or direct release compositions can be formulated, e.g. liposomes, micelles, microparticles, nanoparticles, microspheres, nanospheres or those wherein the active compound is protected with differentially degradable coatings, such as by microencapsulation, multiple coatings, etc. It is also possible to freeze-dry the compounds of the application and use the lypolizates obtained, for example, for the preparation of products for injection.

The compounds may be administered to a subject alone or in combination with pharmaceutically acceptable carriers, as noted above, the proportion of which is determined by the solubility and chemical nature of the compound, chosen route of administration and standard pharmaceutical practice.

The dosage of the compounds and/or compositions described herein can vary depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the subject to be treated. One of skill in the art can determine the appropriate dosage based on the above factors.

Oral preparations of low-dose haloperidol may be formulated, preferably as tablets, capsules, or drops, containing from 0.05-2 milligrams, suitably 0.1-0.5 milligrams, more suitably 0.2, 0.3 or 0.4 milligrams of haloperidol described herein, per dosage unit. The compounds described herein may be administered initially in a suitable dosage that may be adjusted as required, depending on the clinical response.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The following Examples are set forth to aid in the understanding of the invention, and are not intended and should not be construed to limit in any way the invention set forth in the claims which follow thereafter

EXAMPLES

Example 1

Administration of Low Dose Haloperidol to Rats

The customary dose of haloperidol in treating psychosis in humans is between 5 mg/day and 20 mg/day on a continuing basis. These therapeutic doses are known to occupy between 60% and 70% of dopamine D2 receptors in the human brain, as revealed by positron emission tomography. In the rat, the human dose of 5-20 mg/day of haloperidol corresponds to 0.04-08 mg/kg (S. Kapur, S. C. Vanderspek, B. A. Brownlee, J. N. Nobrega, Antipsychotic dosing in preclinical models is often unrepresentative of the clinical condition: A suggested solution based on in vivo occupancy. J. Pharmacol. Exper. Therap. 305: 625-631, 2003).

However, a surprising finding was that using haloperidol doses in rats of 0.03 mg/kg down to 0.005 mg/kg, which are much lower than those used clinically, results in levels or proportions of $D2^{High}$ receptors that were moderately elevated by two-fold. Such animals exhibited heightened locomotion and active exploration analogous to increased curiosity and increased well-being in humans. For example, the data in the following Table 1 shows that 0.005 mg/kg of haloperidol (i.p.) in rats elicits a two-fold increase of $D2^{High}$ receptors between 3 and 5 days.

The data in Table 1 illustrate that a very low dose of haloperidol, 0.005 mg/kg, elevates $D2^{High}$ receptors approximately two-fold over a matter of 3-5 days. On days 3-5 or upon stopping the haloperidol, these rats showed spontaneously increased locomotion and well-being insofar as they groomed themselves more actively. These data indicate an antidepressant or procognitive effect of low-dose haloperidol, either on or withdrawn from the drug.

The data with haloperidol are only an example of the general phenomenon that occurs with other antipsychotics. For example, using doses that are 10% of the usual antipsychotic doses given to rats, the following drugs (given daily i.p. for 9 days) elevated the control proportion of 20% for $D2^{High}$ to interpolated values 30-45% (clozapine, 3.5 mg/kg), 35-40% (olanzapine, 0.075 mg/kg), 40% (olanzapine, 0.075 mg/kg) and 40% (quetiapine, 2.5 mg/kg).

Moreover, the increased level of $D2^{High}$ to 40% is associated with active exploratory behavior in such rats. For example, in a series of rats (one month after birth) that had been selected on the basis of their spontaneous exploratory behavior into high- and low-curiosity, the low-curiosity animals revealed a level of $D2^{High}$ that averaged 22.5±1.5%, compared to the high-curiosity animals that revealed a $D2^{High}$ level of 43.8±4.4% (Table 2), without any overlap occurring.

Therefore, the data in Tables 1 and 2 indicate that a two-fold increase in $D2^{High}$ results in a more active, more curious, more motivated, and "less depressed" rat.

Example 2

Competitive Binding Assays

The method for measuring the proportion of D2 receptors in the high-affinity state is as follows. (The general method is also used for measuring the competitive potency of a compound at any particular receptor).

After $CO_2$ euthanasia, rat brains are immediately removed, and the striata dissected and frozen at $-80°$ C. until used. The striata are homogenized in buffer (4 mg frozen striatum per ml buffer consisting of 50 mM Tris-HCl [pH 7.4 at 20° C.], 1 mM EDTA, 5 mM KCl, 1.5 mM $CaCl_2$, 4 mM $MgCl_2$; 120 mM NaCl), using a Teflon-glass homogenizer, with the piston rotating at 500 rpm, and 10 up and down strokes of the glass container. The homogenate is not washed because it is known that 30-50% of the D2 receptors can be lost by this procedure.

[$^3$H]Domperidone is custom synthesized as [phenyl-$^3$H (N)]domperidone (42-68 Ci/mmol) by PerkinElmer Life Sciences Inc., Boston, Mass., and used at a final concentration of 2 nM. The dissociation constant, Kd, for [$^3$H]domperidone is 0.47 nM at dopamine D2 receptors in rat striatum.

The proportion of $D2^{High}$ receptors in the striata is measured by the competition of dopamine with 2 nM [$^3$H]domperidone, as follows. Each incubation tube ($12 \times 75$ mm, glass) receives, in the following order, 0.5 ml buffer (containing dopamine at various concentrations, with or without a final concentration of 10 µM S-sulpiride to define nonspecific binding to the dopamine D2 receptors), 0.25 ml [$^3$H]domperidone, and 0.25 ml of the striatal homogenate. The tubes, containing a total volume of 1 ml, are incubated for 2 h at room temperature (20° C.), after which the incubates are filtered, using a 12-well cell harvester (Titertek, Skatron, Lier, Norway) and buffer-presoaked glass fiber filter mats (Whatman GF/C). After filtering the incubate, the filter mat is rinsed with buffer for 15 s (7.5 ml buffer). The filters are pushed out and placed in scintillation polystyrene minivials (7 ml, $16 \times 54$ mm; Valley Container Inc., Bridgeport, Conn.). The minivials receive 4 ml each of scintillant (Research Products International Corp., Mount Prospect, Ill.), and are monitored 6 h later for tritium in a Beckman LS5000TA scintillation spectrometer at 55% efficiency. The specific binding of 2 nM [$^3$H] domperidone is defined as total binding minus that in the presence of 10 µM S-sulpiride. The high-affinity phase occurs between 1 and 100 nM dopamine, while the low-affinity phase occurs between 100 and 10,000 nM dopamine. The two phases are clearly and consistently demarcated, not requiring computer-assisted resolution of the data into high- and low-affinity components. Moreover, the proportion of D2 receptors in the high-affinity phase between experiments is very consistent, further obviating the need for computer-assisted analysis.

The Cheng-Prusoff equation (Cheng and Prusoff, 1973) is used to derive the dissociation constant (Ki value) of dopamine from the concentration that inhibited 50% of the high-affinity component ($IC_{50}$) or 50% of the low-affinity component in the dopamine/[$^3$H]domperidone competition curve. The form of the Cheng-Prusoff equation used was $Ki=IC_{50}/(1+C/Kd)$, where C was the final concentration of the ligand and Kd was the dissociation constant of [$^3$H]domperidone, as determined directly by independent experiments of saturation binding to the tissue (i.e., Scatchard plot).

Although cloned receptors are used for the studying the properties of receptors other than D2, rat brain tissues are used to examine the high-affinity states of receptors.

The cloned dopamine D1 receptor is measured using a final concentration of 1.25 nM [$^3$H]SCH23390 (Kd was 0.5 nM) and using 1 µM (+)-butaclamol to define nonspecific binding.

Competition at the cloned dopamine D3 receptors is done using 2 nM [$^3$H]raclopride (Kd was 1.6 nM) and using 10 µM S-sulpiride to define nonspecific binding.

Competition at the muscarinic receptors is done using either the cloned M1 receptors or the rat frontal cortex, 0.6 nM [$^3$H]QNB, and using 200 nM atropine to define nonspecific binding.

Competition at the cloned serotonin-1A receptors is done with 1.4 nM [$^3$H]8-OH-DPAT (Kd was 1.5 nM) and using 100 µM serotonin to define nonspecific binding.

Competition at the serotonin-2A receptors is done using either rat frontal cerebral cortex tissue or cloned serotonin-2A receptors, 1 nM [$^3$H]ketanserin and using 10 µM serotonin to define nonspecific binding.

Competition at alpha-1-adrenoceptors is done using rat cerebral cortex tissue, 1.5 nM [$^3$H]prazosin and using 10 µM adrenaline to define nonspecific binding.

Competition at alpha-2A-adrenoceptors is done using human cloned rat receptors (in Sf9 cells), 2.1 nM [$^3$H]yohimbine and using 100 µM adrenaline to define nonspecific binding.

Competition at beta-adrenoceptors is done using rat cerebral cortex tissue, 0.5 nM [$^3$H]dihydroalprenolol and using 200 nM propranolol to define nonspecific binding.

The compound dissociation constant, K, is calculated as usual as $C50\%/[1+C^*/Kd]$, where $C50\%$ is the drug concentration which inhibits ligand binding by 50%, where $C^*$ is the ligand concentration, and where Kd is the dissociation constant of the ligand, as obtained from a separate experiment using a range of ligand concentrations.

Using the in vitro methods outlined above, the potencies of haloperidol at the various receptors are:

Ki at dopamine D2 receptor (clone): 0.7 nM

Ki at alpha-adrenoceptor (rat cortex): 6.1 nM

Ki at serotonin-2A receptor (rat cortex): 37 nM

Ki at muscarinic receptor (rat cortex): >10,000 nM

Ki at dopamine D1 receptor (rat striatum): 55 nM

Ki at alpha-2A-adrenoceptor (clone): 600 nM

Ki at histamine-1 receptor (rat cortex): 366 nM

The fraction of D2 receptors occupied, f, is given by $f=C/(C+Ki)$, where C is concentration of haloperidol in the plasma water or spinal water in a treated patient, and where Ki is the dissociation constant of haloperidol, 0.7 nM, at the D2 receptor.

When using low-dose haloperidol, say 0.4 mg per day, the plasma water concentration of haloperidol is expected to be between one-twentieth to one-tenth the concentration (0.075 to 0.15 nM) that elicits antipsychotic action, namely 1.5 nM in plasma water or spinal fluid water.

Therefore, at a dose of 0.4 mg haloperidol per day, the fraction of D2 receptors expected to be occupied would be 0.1 nM/(0.1 nM+0.7 nM) or ~12%.

Therefore, the present proposed use of low-dose haloperidol would occupy approximately 5% or 10% of D2 receptors, sufficient for antidepressant action but not sufficient for either antipsychotic action or to elicit parkinsonian signs.

Example 3

Preliminary Clinical Observation of Patients with Depression Following 7 Days Low-Dose Haloperidol Treatment In order to assess the effect of low-dose haloperidol on patients with depression, clinical observations were conducted on a small group of patients with depression who were administered low-dose haloperidol and then observed for a period of time following dosing.

All subjects were patients of a clinic for treatment-resistant depression at a tertiary hospital. Treatment-resistance was defined as a treatment failure on at least two other antidepressants prior to their referral to the clinic. Patients were deemed to be depressed by the referring psychiatrist as well as the treating psychiatrist according to DSM IV Criteria for Major Depressive Disorder. All patients were assessed by the Hamilton Scale for Depression (HAMD) during each visit (Hedlung and Vieweg, Journal of Operational Psychiatry, 1979, 10:149-165). Weekly appointments were scheduled and the majority of patients were compliant with these weekly assessments. All patients were maintained on their current antidepressants and low dose haloperidol was used as an augmenting agent given once daily for a week. Only one subject was treated with low dose haloperidol without other antidepressants.

A seven-day regimen of low-dose haloperidol was provided to human patients as follows: 0.2 mg on day 1, 0.2 mg on day 2, 0.25 mg on day 3, 0.25 mg on day 4, 0.25 mg on day 5, 0.3 mg on day 6 and 0.3 mg on day 7, followed by a complete cessation of the medication.

The results are shown in Table 3, where the values are based on the Hamilton depression scale (Hedlung and Vieweg, Journal of Operational Psychiatry, 1979, 10:149-165). The higher the value, the more severe the depression. In all patients, the severity of the depression had decreased after the 7-day treatment regimen with low-dose haloperidol.

The results of this observation indicate that patients treated with a daily regimen of low-dose haloperidol showed improvement in their symptoms of depression.

Example 4

A Pilot Placebo-Controlled, Double-Blind, Randomized Parallel Group Study to Evaluate the Efficacy of Treatment with Low-Dose Haloperidol (Prophetic Example)

The study is a randomized, double blind, placebo-controlled, parallel group design. Male and female subjects (18-65 years) suffering from an MDE will be recruited. At screening, subjects will have a medical history recorded and laboratory pathology (ECG, clinical chemistry, hematology and urinalysis) assessed. Subjects who are on antidepressants will have a one week washout period (28 days for fluoxetine or 14 days for irreversible MAO inhibitors).

Subjects with a HAMD17 ≥14 at screening and randomization, and who satisfy all inclusion and exclusion criteria will be eligible to continue in the study. Those who fail to fulfill the criteria will be provided standard medical care as necessary.

At Visit 2, subjects will be randomized in a 1:1 ratio to receive either low dose haloperidol or placebo in a double blind fashion. After 7 days, all subjects will return to the clinic for Visit 3, and will continue with placebo medication for 28 days. Subjects will return to the clinic weekly for visits 4, 5, 6 and 7 during this observation period. The treatment blind will be maintained throughout the study.

Study medication will be administered as 1 oral capsule once daily in the evening before bed. At Visit 2 (when all lab tests results have been reviewed and when the washout period is completed), subjects will be randomly assigned to one of two treatment groups: haloperidol (0.25 mg/day) or placebo. They will receive a blister pack of ten (10) capsules for week 1 (one for each day, with three (3) additional capsules in case the next appointment is delayed). At visit 3, all subjects will be on placebo for the remainder of the trial and will receive blister packs of 10 placebo capsules at each weekly visit (labeled week 2, 3, 4 or 5). The visits will be weekly. There will be a minimum of seven (7) days (maximum 10 days) between visits 2 and 3. Thereafter, weekly visits will have a range of 5-10 days from the last visit. Subjects will be instructed to return their blister packs so that compliance can be ascertained.

The following are inclusion criteria for patients to enter the study: male or female subjects 18-65 years; single episode or recurrent MDD (to a maximum of 5 prior episodes);no current therapy for depression as per washout instructions; able to provide written informed consent; meet criteria for MDD with current MDE, as defined by DSM-IV TR; HAMD17 score ≥14 at screening (visit 1) and baseline (Visit 2; Randomization); change in HAMD score from Visit 1 to Visit 2 (Baseline) of no greater than 20% (only assessed at Visit 2); able to understand and complete questionnaires, and communicate with the investigator and study coordinator; judged to be reliable to keep all appointments and procedures required by the protocol; female subjects of childbearing potential (who are not at least 2 years postmenopausal or surgically sterile or totally abstinent) must be using a reliable, medically acceptable form of contraception and must agree to continue such use throughout the duration of the study; reliable forms of contraception include oral, implanted, transdermal or injected contraceptives, intrauterine devices, and adequate double barrier methods including use of spermicide; partner's vasectomy is also an acceptable contraceptive regimen.

The following are exclusion criteria; Investigators and immediate family members; treatment within the last 90 days with a drug that had not received regulatory approval at the time of study entry; persons who had previously withdrawn from this study or previous study investigating low-dose haloperidol; any known current DSM-IV diagnosis other than MDD, including bipolar disorder, any form of psychotic disorder, or dysthymic disorder over the last 2 years duration; a primary diagnosis of Panic Disorder, Social Anxiety Disorder, Obsessive-Compulsive Disorder within the past year; the presence of an Axis II disorder, which, in the opinion of the investigator, would interfere with compliance in the study; history of active substance dependence within the last half-year, excluding nicotine and coffee, or active substance abuse that may interfere with the outcome of the study as judged by the investigator; acute suicidal ideation or risk, ≥3 on HAMD17 suicide item; serious concomitant diseases such as cancer, serious metabolic (e.g. Insulin dependent diabetes), renal, cardiac, thyroid, immunological, neurological or other significant disease or laboratory abnormality (hematology, blood chemistry, ECG), or treatment for medical conditions which may interact with haloperidol; women who are pregnant or breast-feeding, or men or women who plan to conceive a child during the study period; infirmities or living in an area limiting participation in the study or compliance with study procedures.

Primary Efficacy Analyses—Grid HAMD

The primary objective is to estimate the effects of low-dose haloperidol versus placebo, on the change from baseline to visit 3, 4, 5, 6, and 7 on the HAMD-17. For this primary endpoint, the treatment differences for the treatment group versus the placebo group is determined using a one-way analysis of variance (ANOVA) model with treatment group as a factor. The point estimate of the difference between the active group and placebo, as well as the 95% confidence interval for the difference, is estimated.

Secondary Analysis Clinical Global Impression Score

Changes in CGI-S score from randomisation to visits 3, 4,5,6,7 is analysed using an ANCOVA model, following the same conventions as the primary analysis. Baseline CGI-S score is used as a covariate in the model. The interest separately focuses on the treatment differences between low-dose haloperidol and placebo. Model based point estimates and 95% confidence intervals are reported. P-value is reported for the comparison between low-dose haloperidol and placebo.

The dichotomized CGI-I score (much/very much improved as one category against the other categories) at visits 3, 4, 5, 6, 7 is analysed using logistic regression. The models include treatment and centre as explanatory variables. The interest separately focuses on the treatment differences between low-dose haloperidol and placebo. Model-based point estimates of odds ratios and 95% confidence intervals is reported. P-value is reported for the comparison between low-dose haloperidol and placebo.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

Proportion of $D2^{High}$ receptors in rat striata

| Day | 0.005 mg/kg | 0.03 mg/kg |
| --- | --- | --- |
| 0 (control) | 19 ± 1% | 19 ± 1% |
| 1 day | interpolated 25% | 28.5 ± 1% |
| 2 days | interpolated 26% | 34 ± 1% |
| 3 days | 32 ± 1% | 57 ± 2% |
| 5 days | 50% | not done |

TABLE 2

| | % $D2^{High}$ | |
| --- | --- | --- |
| | Low-curiosity rats | High-curiosity rats |
| | 19% | 35% |
| | 28% | 38% |
| | 15% | 61% |
| | 22% | 39% |
| | 26% | 38% |
| | 26% | 65% |

TABLE 2-continued

| | % $D2^{High}$ | |
| --- | --- | --- |
| | Low-curiosity rats | High-curiosity rats |
| | 20% | 30% |
| | 24% | 44% |
| Average ± SE | 22.5 ± 1.5% | 43.8 ± 4.4% |

TABLE 3

| Subject | Rating before haloperidol 7-day regimen | Rating after end of haloperidol (weeks after starting medication) |
| --- | --- | --- |
| A | 14 | 9 ($5^{th}$ week) |
| B | 18 | 15 ($5^{th}$ week) |
| C | 30 | 12 ($5^{th}$ week) |
| D | 40 | 32 ($5^{th}$ week) |
| E | 23 | 7 ($4^{th}$ week) |
| F | 20 | 4 ($5^{th}$ week) |
| G | 24 | 13 ($5^{th}$ week) |

The invention claimed is:

1. A method of treating depression comprising administering, to a subject in need thereof, an amount of haloperidol that is effective to elevate amounts of the high affinity state of the dopamine D2 receptor, inducing receptor supersensitivity, wherein the haloperidol is administered orally at a dosage of 0.05 mg to 0.5 mg each day for 3, 4, 5, 6, 7, 8, 9 or 10 consecutive days.

2. The method according to claim 1, further comprising stopping administration of the haloperidol after receptor supersensitivity is induced, followed by restarting administration of the haloperidol after a time sufficient for receptor supersensitivity to decrease and, optionally, repeating the stopping and restarting administration cycle for a period of time effective to treat the depression.

3. The method according to claim 2, comprising
   (a) 3, 4, 5, 6, 7, 8, 9 or 10 days dosing with the haloperidol followed by 1, 2, 3, 4, 5, 6, 7, 8, 9 or 1 days of dosing with placebo;
   (b) 6, 7, 8, 9 or 10 days dosing with the haloperidol followed by 6, 7, 8, 9 or 10 days of dosing with placebo; or
   (c) 7, 8 or 9 days dosing with the haloperidol followed by 7, 8 or 9 days of dosing with placebo; and
   (d) optionally repeating (a), (b) or (c) for a period of time effective to treat the depression.

4. The method according to claim 1, wherein D2 receptor occupancy after administering the amount of the haloperidol that is effective to elevate dopamine $D2^{High}$ receptor amounts, inducing dopamine supersensitivity, is about 2%-10%, 11%-15%, 16%-20% or 20%-25%.

5. The method according to claim 1, wherein the haloperidol is administered for 7 days as follows: 0.2 mg on day 1, 0.2 mg on day 2, 0.25 mg on day 3, 0.25mg on day 4, 0.25 mg on day 5, 0.3 mg on day 6 and 0.3 mg on day 7 , followed by a complete cessation of the medication until a repeat treatment is clinically indicated.

6. The method according to claim 1, wherein 0.25 mg of haloperidol is administered for 7 days followed by a complete cessation of haloperidol until a repeat treatment is clinically indicated.

* * * * *

UNITED STATES PATENT AND TRADEMARK OFFICE
CERTIFICATE OF CORRECTION

PATENT NO. : 8,791,138 B2  
APPLICATION NO. : 12/863513  
DATED : July 29, 2014  
INVENTOR(S) : Seeman et al.

Page 1 of 1

It is certified that error appears in the above-identified patent and that said Letters Patent is hereby corrected as shown below:

On the title page, item [75] Philip M. "Tokeikis" should read -- Philip M. "Toleikis" --.

In the Specification

Column 1, line 54, "PSTS" should read -- "PTSD" --.

Column 3, line 18, "Although," should read -- "Although" --.

Column 4, line 9, "Anorexia nervosa," should read -- "Anorexia nervosa" --.

In the Claims

Column 26, Claim 3, line 39, "1, 2, 3, 4, 5, 6, 7, 8, 9 or 1 days" should read -- "1, 2, 3, 4, 5, 6, 7, 8, 9, or 10 days" --.

Column 26, Claim 5, line 54, "day 7 ," should read -- "day 7," --.

Signed and Sealed this  
Twenty-fifth Day of November, 2014

Michelle K. Lee  
*Deputy Director of the United States Patent and Trademark Office*